(12) United States Patent
Huang et al.

(10) Patent No.: US 7,498,412 B2
(45) Date of Patent: Mar. 3, 2009

(54) PROCESS FOR PREPARING POROUS COLLAGEN MATRIX FROM CONNECTIVE TISSUE

(75) Inventors: Lynn L. H. Huang, Tainan (TW);
Gin-Mol Liu, Tainan (TW)

(73) Assignee: National Cheng Kung University

( * ) Notice: Subject to any disclaimer, the term of this patent is extended or adjusted under 35 U.S.C. 154(b) by 229 days.

(21) Appl. No.: 11/371,323

(22) Filed: Mar. 8, 2006

(65) Prior Publication Data

US 2006/0235205 A1   Oct. 19, 2006

Related U.S. Application Data (63) Continuation-in-part of application No. 10/223,593, filed on Aug. 15, 2002, now abandoned.

(30) Foreign Application Priority Data

Aug. 17, 2001 (TW) .............................. 90120276 A (51) Int. Cl.
*A61K 38/17* (2006.01)
*C07K 14/00* (2006.01)
*A61L 15/16* (2006.01)

(52) U.S. Cl. ...................... 530/356; 530/406; 530/412; 530/419; 530/420; 530/427; 424/444; 424/484

(58) Field of Classification Search ................. 530/356, 530/406, 412, 419, 420, 427; 424/444, 484
See application file for complete search history.

(56) References Cited

U.S. PATENT DOCUMENTS

| 3,368,911 A | 2/1968 | Eloise Kuntz et al. |
| 4,193,813 A | 3/1980 | Chvapil |
| 4,274,410 A | 6/1981 | Chvapil |
| 4,320,201 A | 3/1982 | Berg et al. |
| 4,412,947 A | 11/1983 | Cioca |
| 4,522,753 A | 6/1985 | Yannas et al. |
| 4,948,540 A | 8/1990 | Nigam |
| 4,970,298 A | 11/1990 | Silver et al. |
| 5,019,087 A | 5/1991 | Nichols |
| 5,116,552 A | 5/1992 | Morita et al. |
| 5,336,616 A | 8/1994 | Livesey et al. |
| 5,869,080 A | 2/1999 | McGregor et al. |
| 5,993,844 A | 11/1999 | Abraham et al. |

FOREIGN PATENT DOCUMENTS

| WO | 98/22153 | 5/1998 |
| WO | 99/13902 | 3/1999 |

OTHER PUBLICATIONS

English Abstract of RU 2059383 dated May 10, 1992.

*Primary Examiner*—Jon P Weber
*Assistant Examiner*—Abdel A Mohamed
(74) *Attorney, Agent, or Firm*—Fei-Fei Chao; Andrews Kurth, LLP (57) ABSTRACT

The subject invention provides a process for preparing a porous collagen matrix from connective tissue, said process comprising: a porous structure forming step to treat said connective tissue with poring agent in situ; and a washing step to remove the impurity from said porous connective tissue thereby obtaining a porous collagen matrix.

20 Claims, 5 Drawing Sheets

PROCESS FOR PREPARING POROUS COLLAGEN MATRIX FROM CONNECTIVE TISSUE

RELATED APPLICATION

The present invention is a Continuation-in-Part (CIP) of U.S. patent application Ser. No. 10/223,593 filed on Aug. 15, 2002, now abandoned, which claims the priority of Taiwanese Application No. 090120276, filed on Aug. 17, 2001, which are herein incorporated by reference.

FIELD OF THE INVENTION

The subject invention relates to a process for preparing a porous collagen matrix from connective tissue and a porous collagen matrix prepared by said process.

BACKGROUND OF THE INVENTION

Collagen is a biodegradable protein and exists in a form of fibers in connective tissue of most animals. The primary function of collagen is to maintain the integrity of tissues and to provide tensile strength essential to tissues. Collagen molecule is a biological macromolecule composed of three polypeptide chains that twist around one another. Each polypeptide is composed of about one thousand amino acids, wherein the primary amino acids are glycine, proline and hydroxyproline. At present, more than 21 different types of collagen have been discovered.

For applications, collagen can be manufactured in different forms, such as sponge, gel, tube, sheet, etc. They can be applied as hemostats, wound dressings, drug carriers, scaffolds of artificial organs, fillers to recover tissues, microcarriers and macrocarriers for supporting cell growth, etc. In order to make the above referred collagen matrix exist a porous structure to facilitate cell migration, cell growth or encapsulation and release of drugs, collagen is usually isolated from connective tissue and fabricated into a porous matrix through a lyophilization step. Generally, the matrix is treated with a cross-linking agent or is mixed with a polymer or a polysaccharide prior to or subsequent to the lyophilization step.

The preparation of porous collagen matrix has been disclosed in many prior art patents. For instance, in U.S. Pat. No. 4,193,813, comminuted collagen at pH 3.5 to pH 6.5 is crosslinked with glutaraldehyde followed by freezing at 0 to −20° C. After thawing, the water of the frozen material is eliminated to form a sponge matrix. The pore size of the matrix formed by this process is about 80~1400 μm.

U.S. Pat. No. 4,412,947 relates to a process that pure insoluble particulate collagen is suspended in a weak aqueous organic acid solution followed by freezing at −60 to −70° C. with a temperature reduction rate of −0.3 to −0.4° C. per minute, and then lyophilized to form a porous collagen sheet. U.S. Pat. No. 4,522,753 relates to a process of mixing collagen and chrondroitin sulfate to form a copolymer material. The material is then cross-linked by glutaraldehyde and lyophilized to form a porous matrix with a pore size of 20~180 μm. Such matrix can be used as a basic material of synthetic skin grafts.

U.S. Pat. No. 4,970,298 discloses a collagen matrix prepared by dispersing collagen in an acidic solution or by mixing the collagen dispersion with hyaluronic acid and fibronectin. The dispersion is frozen at the different temperatures and then lyophilized to form a porous sponge. The sponge is cross-linked with a carbodiimide or by a dehydrothermal process. The freezing temperature is −30° C. to −50° C. The pore size of the matrix obtained is about 20~250 μm. The collagen matrix containing hyaluronic acid or fibronectin exhibits a pore size of 100~150 μm.

U.S. Pat. No. 4,948,540 describes a process that involves freeze-drying the mixture of native collagen and soluble collagen fibers and compressing at a pressure of 15,000~30,000 p.s.i. The material is then cross-linked by dehydrothermal method to obtain a final product which is a sheet material with high absorptivity.

U.S. Pat. No. 5,116,552 describes a process for preparing a crack-free sponge matrix. An acidic collagen solution is frozen at −40° C. and lyophilized into a sponge. The sponge is then incubated at 105° C. for 24 hours and then cross-linked for 24 hours with glutaraldehyde to form a matrix with a pore size of 50~120 μm. The matrix is then immersed in 15% alcohol. After second lyophilization at a lower temperature of −80° C. or −135° C., a crack-free sponge matrix is obtained.

U.S. Pat. No. 5,869,080 describes a process for preparing an absorbable implant material. A sponge matrix is formed by adding a proper amount of alcohol to the collagen dispersion in sodium hydroxide, pre-freezing it at a low temperature (about −5° C.), adding is ice particles to the dispersion, cross-linking the dispersion with hexamethylene diisocyanate (HMDI), and followed by lyophilizing the dispersion. The matrix obtained by this process exhibits a pore size of 50~400 μm.

U.S. Pat. No. 4,320,201 describes a process for preparing a collagen sponge with a velour-like surface and which is insoluble but highly swellable in water. The making process comprises dehairing animal hides, enzymatically degrading the hides to form a collagen-containing mass, digesting the mass in an acid and/or alkali, swelling the mass in acid, comminuting part of the swollen mass to a fiber, forming a paste in water of about 0.5 to 3 weight % of a mixture which on a dry basis, adjusting the pH to about 2 to 3.5, cross-linking the paste in the presence of a cross-linking agent such as aliphatic, aromatic, or hydroaromatic diisocyanates at a temperature below 0° C. to form a swollen sponge, and removing water by freeze drying.

U.S. Pat. No. 5,019,087 describes a process that preparing a hollow conduit comprises of a matrix of type I collagen and laminin-containing material derived from animal collagenous tissue for promoting the in vivo regeneration of a severed nerve wherein laminin-containing material acts the role of cross linker to support collagen strength. The cleaned and washed collagen containing material has to be comminuted, generally by slicing or grinding in this invention.

WO Patent No. 99/13902 describes a process that preparing dural substitutes with collagen dispersions derived from animal tissues for promoting meningeal tissue growth. Suitable forms for the dural substitutes include a sponge, a film, a non-woven matrix, a felt or a combination of at least two of the foregoing forms. The matrix is a planar object having pores ranging in diameter from about 30 μm to 300 μm wherein the cleaned and washed collagen containing material is comminuted generally by slicing or grinding. In this invention, the enhanced strength of products is accomplished by desired rate of bioresorption which is seen as self-cross linking step.

U.S. Pat. No. 5,993,844 describes a detergent-free and enzyme-free method for the removal of non-collagenous components from native mammalian tissues to yield an essentially collagenous matrix that maintains its structure integrity. Although the process uses alkaline/cheating agent solution and acid solution containing salt to remove cells and to relax the collagen fiber, the matrix doesn't have the characteristic of porous structure.

U.S. Pat. No. 5,336,616 discloses a method for processing and preserving an acellular collagen-based tissue matrix for transplantation. The method includes the steps of processing biological tissues with a stabilizing solution to reduce procurement damage, treatment with a processing solution to remove cells, treatment with a cryoprotectant solution followed by freezing, drying, storage and rehydration under conditions that preclude functionally significant damage and reconstitutions with viable cells. The matrix without alkaline and acid treatment also has no pores.

WO Patent No. 98/22153 describes the collagen webs which are formed in situ by dehydration and cross linking of the insoluble collagen at sites of injuries, and to uses thereof in stimulating epithelial migration to assist wound healing. In this invention, the in situ process must be treated by mechanically dissociate to obtain homogenous colloid and further comprising the cross linking process by drying.

These processes for the preparation of the collagen matrix disclosed in the aforementioned patents comprise complicated operation processes which include comminuting starting materials generally by slicing or grinding, extraction, purification, lyophilization, and further comprising cross-linking process. Acidic or alkaline collagens are generally used and cross-linked by a dehydrothermal process or by some chemical cross-linking agents, and lyophilized to obtain porous collagen matrices. The matrix products obtained by any of these processes exhibits poor porous homogeneity. Furthermore, because most of the chemical cross-linking agents are toxic, the application extent of these processes is limited.

To obtain a better porous homogeneity, to prevent possible toxic effects resulted from the chemical cross-linking agents, to save vast energy on collagen extraction, and yet to obtain a more stable porous network, the subject invention proposes an improved process for manufacturing the excellent porous collagen matrix for collagen-related products and applications.

SUMMARY OF THE INVENTION

The subject invention provides an improved method and products thereof that overcome the disadvantages of the conventional technique for preparing a collagen matrix. Meanwhile, the subject invention provides a collagen matrix product with excellent qualities with unexpected results.

An object of the subject invention is to provide an in situ process, which maintain some structural scaffold of the collagenous tissue matrix, and to utilize said process for preparing a porous collagen matrix from connective tissue.

Another object of the invention is utilizing a porous structure forming step to provide a porous collagen matrix prepared without cross-linking step.

Another object of the invention is utilizing a softening step to provide a porous collagen matrix prepared.

Another object of the invention is utilizing a drying step to provide a porous collagen matrix prepared.

BRIEF DESCRIPTION OF THE DRAWINGS

Additional objects and features of the present invention will become more apparent and the invention itself will be best understood from the following Detailed Description of the Invention, when read with reference to the accompanying drawings.

DETAILED DESCRIPTION OF THE INVENTION

The preferred embodiments of the present invention described below relate particularly to a porous collagen matrix and innovative processes for making same. While the description sets forth various embodiment specific details, it will be appreciated that the description is illustrative only and should not to be construed in any way as limiting the invention. Furthermore, various applications of the invention, and modifications thereto, which may occur to those who are skilled in the art, are also encompassed by the general concepts described below.

The process of the subject invention overcomes the disadvantages of the conventional technique of preparing collagen matrices. The process of the subject invention has the following features and advantages: (i) the cost of manufacturing the porous collagen matrix is substantially reduced; (ii) the preparation time is greatly decreased; (iii) the structure of the matrix is more stable than the conventionally prepared collagen matrix; (iv) the addition of a cross-linking agent is not required; and (v) the collagen matrix prepared by the process of the subject invention can be readily used directly as biomedical materials or scaffolds for tissue engineering.

The connective tissue of animals is rich in collagen. Therefore, the subject invention may directly utilize connective tissue as the starting materials. The source of connective tissue may derive from animals which have connective tissue, such as cattle, pigs, horses, sheep, chickens, ducks, turkeys, gooses, whales, sharks, and the like. The connective tissue suitable for the process of the subject invention includes skin, dermis, subcutaneous tissue, ligament, tendon, aponeurosis, cartilage, bone tissue, cornea, sclera, aorta, vessel, and the like. The following description of dermis treatment is an example of the subject invention. Lipid of fresh animal skin is removed, and then the animal skin is washed a few times with saline. The surface layer of the animal skin is removed with a dermatome, and the dermis with proper thickness is then obtained. The dermis is washed with phosphate buffered saline. Solution retained on the surface of the dermis is removed.

In one embodiment, the in situ operation process of the subject invention utilizes animal connective tissue as starting materials to preparing porous collagen matrix. The in situ operation process of this invention is substantially acellular and free of non-collagenous components while maintaining some structural scaffold of the collagenous tissue matrix. The in situ operation process of the subject invention does not need to mince and/or grind and/or damage intact connective tissue. Then the material is subject to the necessary treatment procedures (such as a porous structure forming step and a washing step or softening step or drying step) to form porous structure.

Therefore, it is some aspects of the subject invention to provide a process for the preparation of a porous collagen matrix. Said porous structure forming step comprises treating connective tissue with a solution of poring agents so as to obtain a porous collagen matrix. Furthermore, the in situ process treating connective tissues can be in the absence of a cross-linking process.

It is another aspect of the subject invention to provide a process for preparing a porous collagen matrix from connective tissue, wherein the process comprises treating connective tissue with a softening solution so as to obtain a porous collagen matrix. Moreover, while the thickness of connective tissue is less than 300 µm, this process may not be necessary.

In one embodiment, the process of the subject invention comprises a softening step by acid treatment to treat-connective tissue so that the connective tissue with a softening solution so that the connective tissue can be softened. The softening solution is suitable for the subject invention and may include organic or inorganic acids, water, or weak bases. Inorganic acids may include, but are not limited to, hydrochloric acid, phosphoric acid, boric acid or sulfuric acid.

Organic acids may include, but are not limited to peracetic acid, formic acid, acetic acid, propanoic acid, butyric acid, pentanoic acid (valeric acid), hexanoic acid (caproic acid), heptanoic acid (enanthic acid), capric acid, oxalic acid, malonic acid, succinic acid, glutaric acid, adipic acid, benzoic acid, and the analogs, or derivatives of the aforementioned acids, such as methylpentanoic acid, 2-hydroxypropanoic acid (lactic acid), chlorohexanoic acid, 4-hydroxy-6-methylheptanoic acid, 2-aminopropanoic acid, 2,3-dihydroxysuccinic acid, butenedioic acid (fumaric acid or maleic acid), methylbenzoic acid, chlorobenzoic acid, hydroxybenzoic acid, phthalic acid, cyclohexane carboxylic acid, methylcyclobutane carboxylic acid, methylcyclohexane carboxylic acid, cyclopentane dicarboxylic acid, etc.

In the softening step of acid treatment, a softening solution with an aforesaid acid is utilized to treat the connective tissue. For instance, a softening solution with acetic acid at a concentration ranging from about 0.01 to 4M is utilized. In that case, dermal tissue is treatment at a temperature between 4 and 45° C. for 1 to 150 hours. In one preferred embodiment of the present invention. A softening solution with hydrochloric acid at a concentration ranging from about 0.01 to 2N is utilized. In that case, dermal tissue is treated at a temperature between 0 and 60° C. for 0.1 to 150 hours.

The softening step of acid treatment, can be carried out in two steps. For instance, dermal tissue is initially treated with an acidic solution at a higher concentration ranging from 0.1 to 6M for 0.1 to 100 hours in a first step, and then with an acidic solution at a lower concentration ranging from of 0.01 to 2M for 1 to 200 hours in a second step. For instance, one of the preferred embodiment of the subject invention is that connective tissue is treated with 1.0M of acetic acid solution on a rotator at 37° C. for 12 hours; then treated connective tissue is placed in 0.2M of acetic acid solution for 72 hours so as to achieve effects of penetration and immersion of acids in both inner and outer parts of the connective tissue.

In the softening step of acid treatment, salts can be added to the softening solution such as an acidic solution so as to stabilize collagen molecules to create a better porous structure in the matrix. For instance, the softening solution containing concentration of the salt is preferably at a concentration ranging from about 0.01 to 4M. Salts suitable for the subject invention include organic or inorganic salts. Inorganic salts may include, but are not limited to, halide salt of alkaline or alkaline earth group, such as sodium chloride or calcium chloride. Organic salts may include, but are not limited to, carboxylates, such as calcium propanoate, sodium benzoate, sodium acetate or sodium carbonate. When 0.1 to 2M of sodium chloride is added to the softening solution, the best effect for stabilizing the connective tissue matrix can be achieved and the best porosity can be obtained. For instance, in the process of the subject invention mentioned above, a collagen matrix with stable and homogeneous pores can be formed if 0.5M of sodium chloride is added to the lower concentration (0.2M) of acetic acid solution.

In one embodiment, the process of the subject invention utilizes a poring agent to treat connective tissue so that pores can be formed inside the connective tissue. The poring agent may include, but are not limited to, oxidants, peroxidants, acids or bases although a peroxidant is preferably selected. For instance, in the process of the subject invention mentioned above, a hydrogen peroxide treatment can simultaneously kill bacteria and produce pores in the matrix. The concentration of hydrogen peroxide solution suitable for the process of the subject invention is 0.1% to 10%, preferably 0.5% to 3.0%. This treatment can be carried out at 0 to 70° C., preferably 4 to 60° C., for 0.1 to 240 hours. Said treatment can be also carried with peracetic acid, $NaClO_4$, periodic acid, perbromic acid, hydroxide or halide containing tertiary amino group, such as d-tubocurarine chloride, choline chloride, muscarine hydroxide, acetylcholine hydroxide, betaine, decamethonium chloride, hexamethonium chloride, etc. In addition, other agents, such as hydriodic acid, trichloromelamine, difluoroacetic acid, chlorine dioxide, polyvinyl pyrrolidone-iodine (povidone-iodine), p-aminosalicylic acid, isonicotinic acid hydrazine, sulfonamides, trimethoprim, metronidazole, 4-quinolone derivatives, imidazole derivatives, azidothymidine, etc., can be used in this step to achieve the effect similar to the hydrogen peroxide treatment.

In one embodiment, the process of the subject invention utilizes a washing solution which is selected from the group consisting of detergent, chelating agent and mixtures thereof. To facilitate porous collagen matrix being directly utilized as artificial skins or tissue scaffolds, the process of the subject invention may further comprise a step of removing non-collagenous substances such as cells, cellular debris, and extraneous matters. Said step utilizes a solution containing a detergent, such as sodium dodecyl sulphate (SDS), Tego compounds (such as Tween 80, Triton W. R. 1339, p-isooctylpolyoxy-ethylene phenol polymer; Triton A20), cetylpyridinium chloride, cetyltrimethyl-ammonium bromide, dioctyl sodium sulphosuccinate, Emasol 4130 (polyoxyethylene sorbitan monoleate), Lubrol W, Nonidet P40, etc. Preferably, a solution containing 0.01 to 10% of SDS can be used to treat the connective tissue at 4 to 45° C. for 1 to 150 hours.

The solution containing a detergent used in the process of the subject invention may further comprise a chelating agent, such as EDTA (ethylene diamine tetra-acetic acid), DOTA (1,4,7,10-tetraazacyclododecane-1,4,7,10-tetraacetic acid), DOTP (1,4,7,10-tetraazacyclododecane-1,4,7,10-tetrakis (methylene phosphonic acid)), CDTA (trans-1,2-diaminocyclohexantetra-acetic acid, Tiron (4,5-dihydroxybenzene-1,3-disulphonic acid, thiourea, 8-hydroxyquinoline-5-sulphonic acid, 3,6-disulpho-1,8-dihydroxynaphthalene, Eriochromeschwarz T (1-(1-hydroxy-2-naphthylazo)-2-hydroxy-5-nitro-4-naphthalene sulphonic acid), ammonium purpurate, etc. For instance, the chelating agent is preferably EDTA with a concentration of 0.01 to 100 mM. Regarding the aforementioned solutions, when the connective tissue is treated with a solution containing only SDS, a collagen matrix with smaller pore size is obtained.

In one embodiment, further comprising the washing process to remove the collagen matrix impurities which may cause antigenic activity. This washing process utilizes an enzyme treatment with a proteolytic enzyme such as ficin, pepsin, and the like, so as to remove impurities. The amount of enzyme added to the collagen matrix and the conditions under which enzyme digestion takes place is dependent upon the particular enzyme being used. The proteolytic enzymes attack the antigenic domain of collagen molecules and non-collagenous impurities, while the main portion of collagen molecules remains preserved in its pure form. There are some occasions that this antigenic removing process may not be necessary while the collagen matrix is to be applied as a tissue substitute wherein the immune reaction is not significant such as in the area of cornea or sclera or wherein an immune stimulant is otherwise preferable such as in the removing area of tumor site.

After the treatments with the aforementioned processes, the connective tissue can be subjected to a drying step which includes, but not limit to, air drying step, low-temperature freezing step and subsequent lyophilizing step under vacuum. In the prior freezing step of lyophilization, the temperature reduction rate and the final freezing temperature are associated with the pore size and homogeneity of the matrix. For example, when the collagen matrix is frozen at $-20°$ C., the homogeneity of pores in the said matrix is more proper for cell ingrowth; when the collagen matrix is frozen at $-80°$ C., the pore size of the matrix is smaller.

It is one object of the subject invention to provide the porous collagen matrices prepared by the aforementioned processes. The porous collagen matrix prepared by the processes of the subject invention can be used in the preparation of artificial tissues/organs or biomedical materials, or used as the media for cell culture.

The following examples are for further illustration of the invention but not intended to limit the invention. Any modifications and applications by persons skilled in the art in accordance with the teachings of the invention should be within the scope of this invention.

EXAMPLE

Example 1

Lipid and fat of pigskin were removed and washed twice. Epidermis of pigskin was removed with a dermatome, and dermal tissue with thickness of 0.2 mm was selected. The dermal tissue was washed with a phosphate buffered saline solution. Solution retained on the surface of the dermal tissue was removed.

Figure 1:
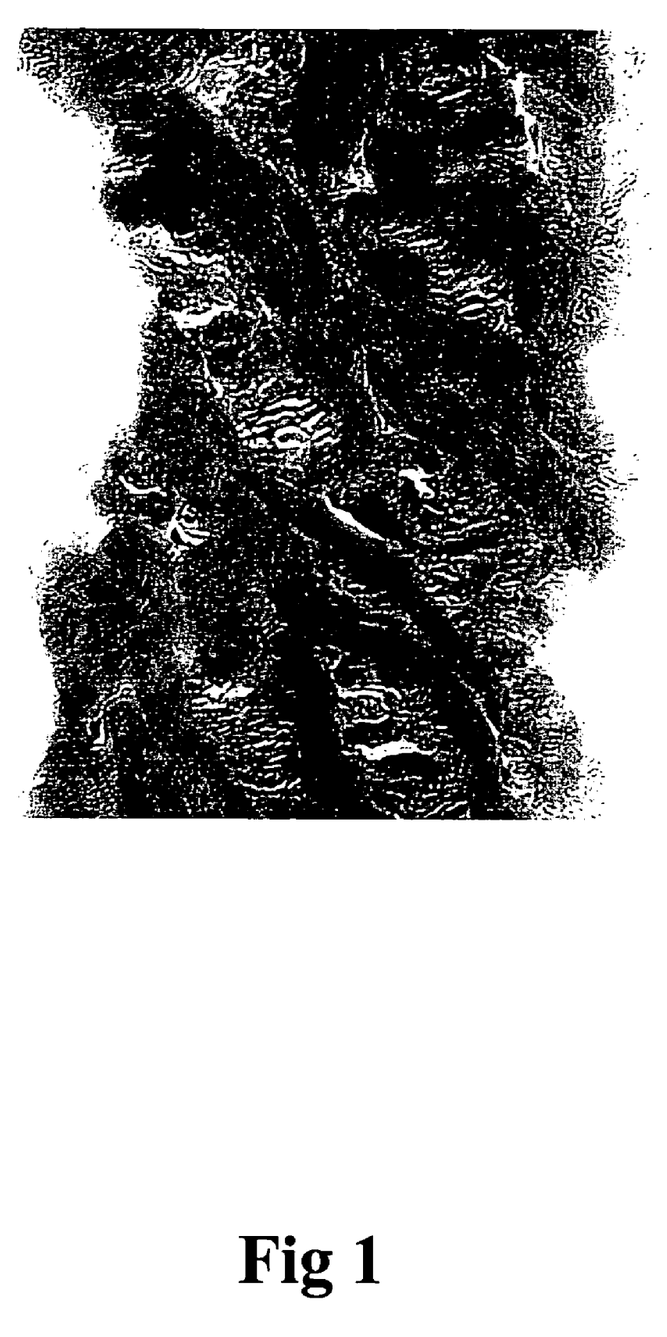
FIG. 1 shows the cross section of the porous collagen matrix prepared by one embodiment of the present invention illustrated in the process of Example 1.

The dermal tissue was then treated with a solution of 3% hydrogen peroxide on a rotator at 37° C. for 24 hours, and then washed with a phosphate buffered saline solution. A porous collagen matrix was obtained and the cross section of the matrix was evaluated and photographed under a light microscope as shown in FIG. 1.

Example 2

Figure 2:
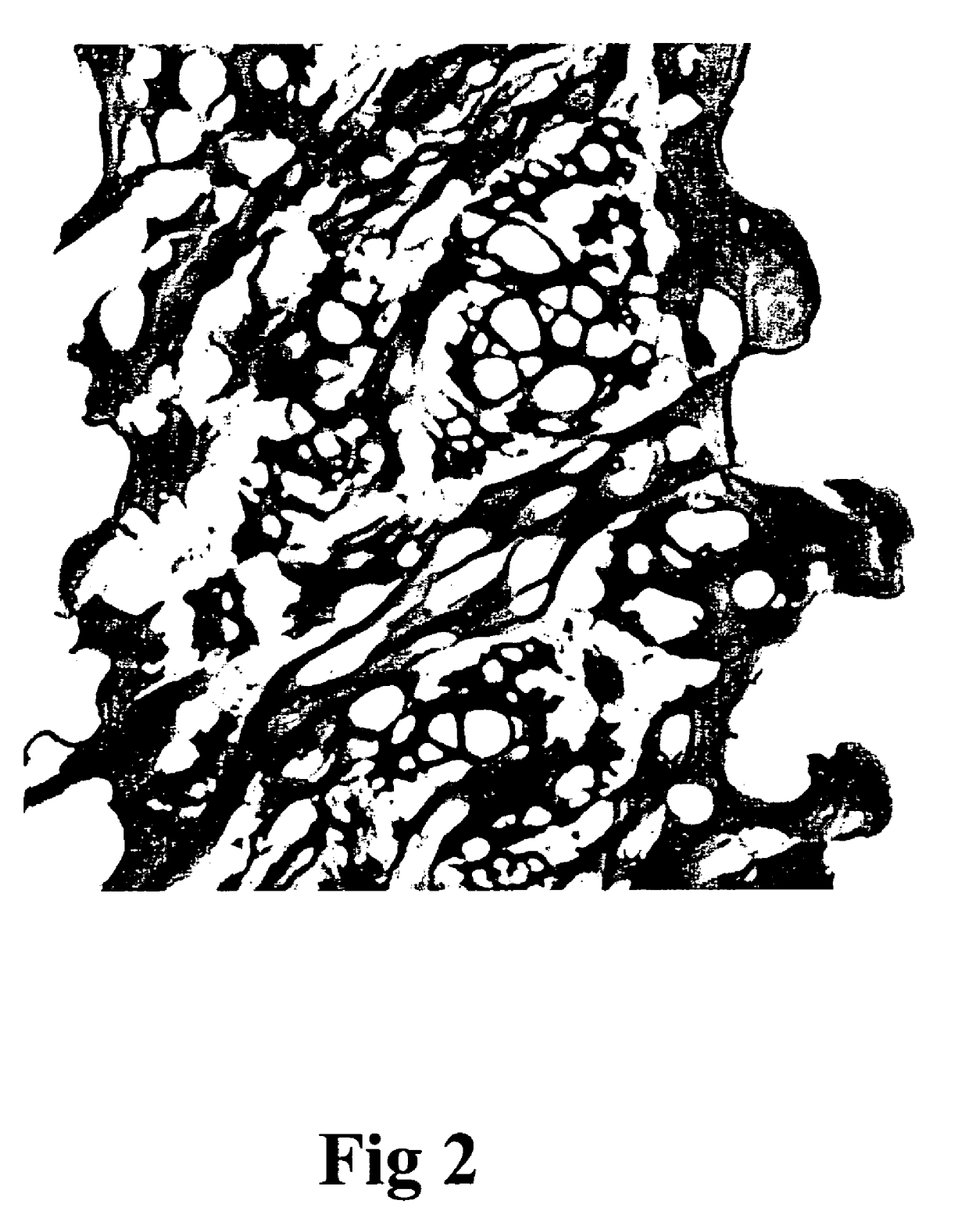
FIG. 2 shows the cross section of the porous collagen matrix prepared by another embodiment of the present invention illustrated in the process of Example 2.

The pig dermal tissue was pre-treated according to the process described in Example 1, and then treated with a solution of 3% hydrogen peroxide. The dermal tissue was then washed with an aseptic phosphate buffered saline solution and frozen at $-20°$ C. with subsequent lyophilization. A porous collagen matrix was obtained and the cross section of the matrix was evaluated and photographed under a light microscope as shown in FIG. 2.

Example 3

Lipid and fat of pigskin were removed and washed twice. Epidermis of pigskin was removed with a dermatome, and dermal tissue with thickness of 0.2 mm was selected. The dermal tissue was washed with a phosphate buffered saline solution containing 0.02% $NaN_3$. Solution retained on the surface of the dermal tissue was removed.

Figure 3:
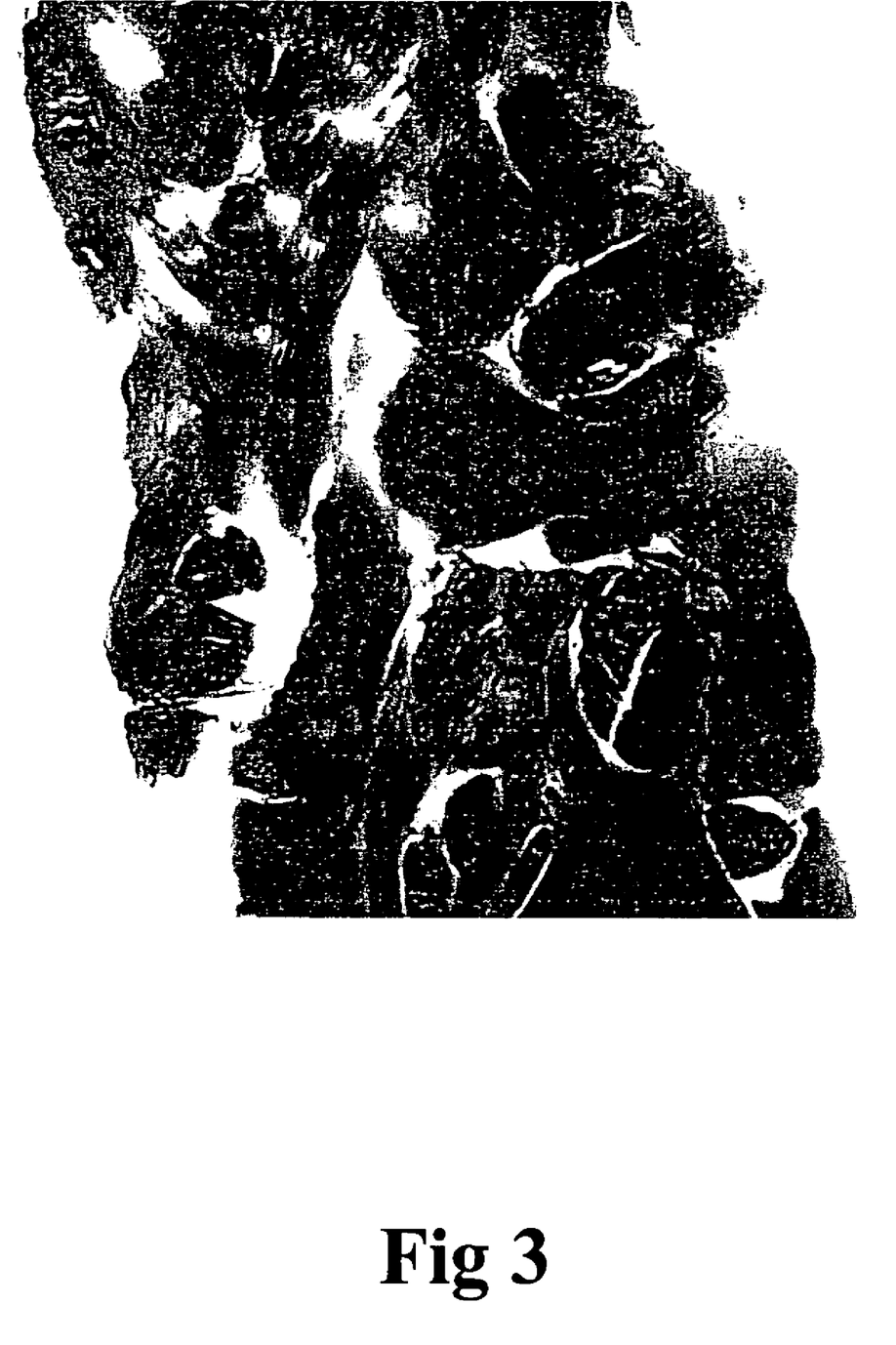
FIG. 3 shows the cross section of the porous collagen matrix prepared by still another embodiment of the present invention illustrated in the process of Example 3.

The dermal tissue was then treated with a solution of 0.5N hydrochloric acid on a rotator at 37° C. for 3 hours. The treated dermal tissue was then washed with an aseptic phosphate buffered saline solution so as to remove residual chemical agents. A porous collagen matrix was obtained and the cross section of the matrix was evaluated and photographed under a light microscope as shown in FIG. 3.

Example 4

Lipid and fat of pigskin were removed and washed twice. Epidermis of pigskin was removed with a dermatome, and dermal tissue with thickness of 0.5 mm was selected. The dermal tissue was washed with a phosphate buffered saline solution. Solution retained on the surface of the dermal tissue was removed.

Figure 4:
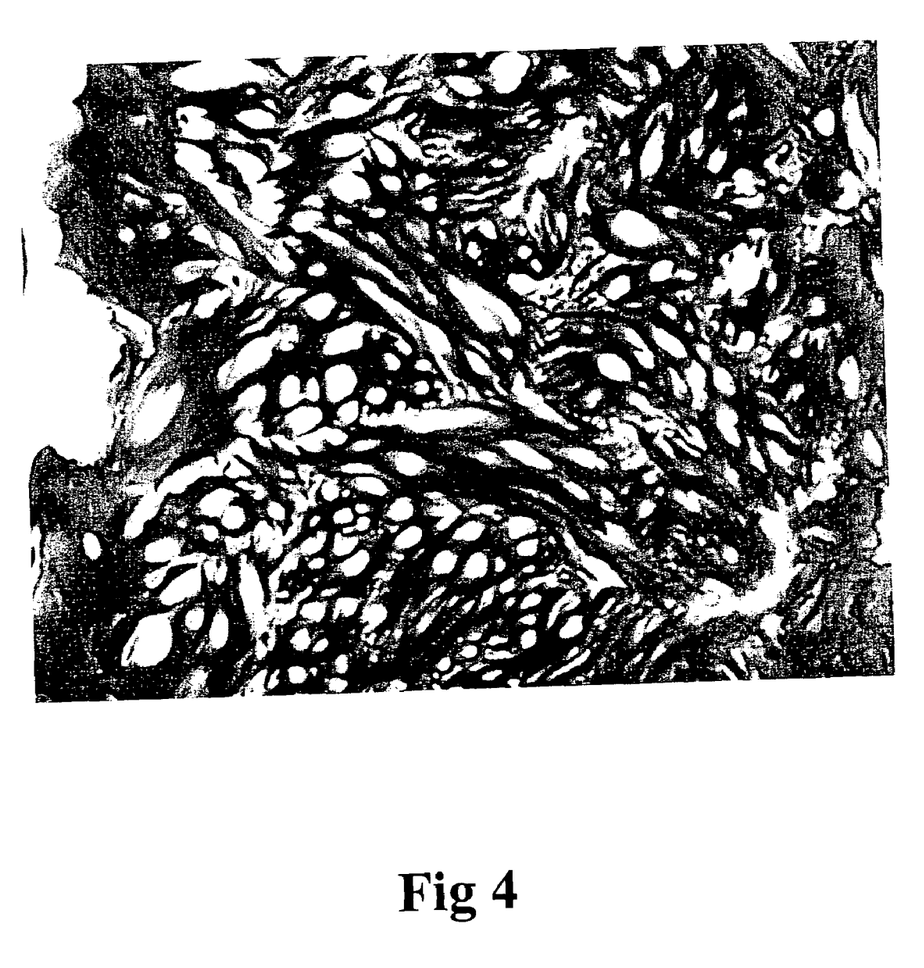
FIG. 4 shows the cross section of the porous collagen matrix prepared by one further embodiment of the present invention illustrated in the process of Example 4.

The dermal tissue was then treated with a solution of 0.5N hydrochloric acid on a rotator at 37° C. for 6 hours. The dermal tissue was then washed with an aseptic phosphate buffered saline solution to remove residual chemical agents. Solution retained on the surface of the dermal tissue was removed. The dermal layer was then frozen at $-20°$ C. with subsequent lyophilization. A porous collagen matrix was obtained and the cross section of the matrix was evaluated and photographed under a light microscope as shown in FIG. 4.

Example 5

Lipid and fat of pigskin were removed and washed twice. Epidermis of pigskin was removed with a dermatome, and dermal tissue with thickness of 0.5 mm was selected. The dermal tissue was washed with a phosphate buffered saline solution. Solution retained on the surface of the dermal tissue was removed.

The dermal tissue was then treated with a softening solution of 1.0M acetic acid on a rotator at 37° C. for 12 hours. The dermal tissue was then transferred to a solution of 0.2M acetic acid containing 0.5M sodium chloride and reacted for 72 hours. After treatment with acetic acid solution, the dermal tissue was transferred to a solution of 1% hydrogen peroxide for reaction for 24 hours and then to a solution containing SDS and EDTA for reaction at 37° C. for 24 hours.

Figure 5:
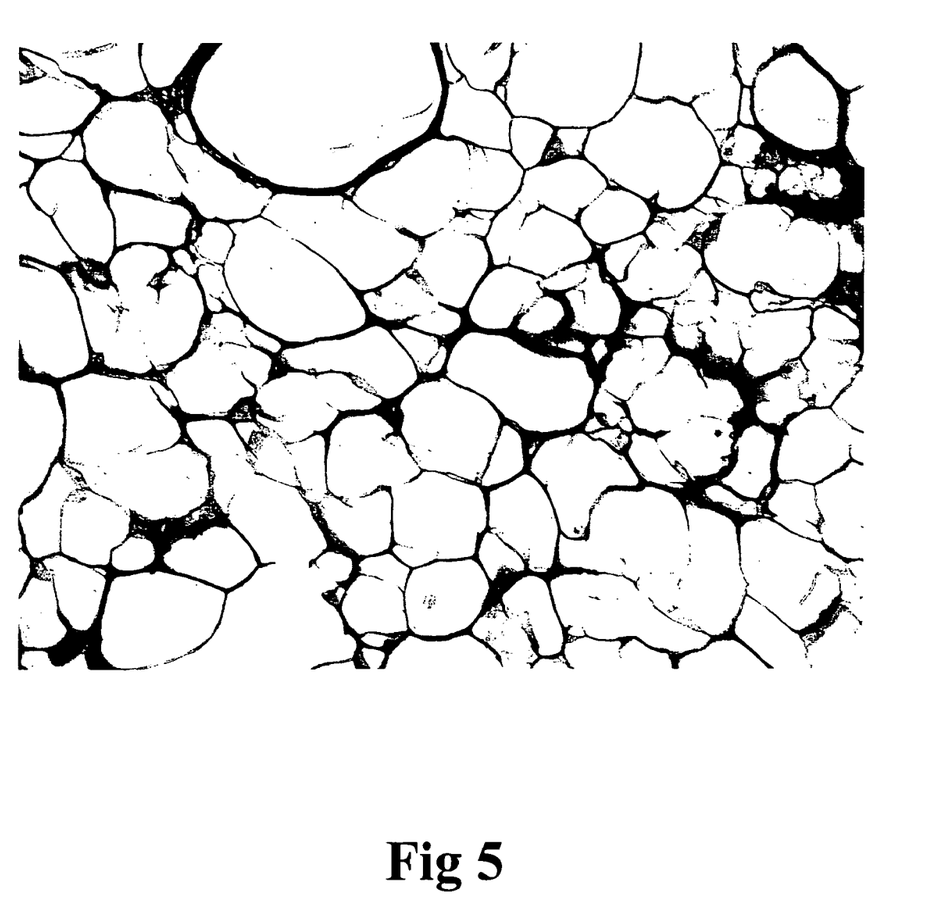
FIG. 5 shows the cross section of the porous collagen matrix prepared by one alternate embodiment of the present invention illustrated in the process of Example 5.

After completing the aforementioned treatments with the chemical solutions, the dermal tissue was washed with aseptic phosphate buffered saline solution to remove the residual chemical agents. The dermal tissue was then frozen at $-20°$ C. with subsequent lyophilization. A porous collagen matrix was obtained and the cross section of the matrix was evaluated and photographed under a light microscope. As shown in FIG. 5, the homogeneity of pores and the pore size of the matrix are very suitable for applications.

Although preferred embodiments of the invention have been described in detail, including a porous collagen matrix and methods of manufacturing thereof, certain variations and modifications is apparent to those skilled in the art, including embodiments that do not provide all of the features and benefits described herein. Accordingly, the scope of the present invention is not to be limited by the illustrations or the foregoing descriptions thereof, but rather solely by reference to the appended claim s

We claim:

1. A process for preparing a porous collagen matrix from connective tissue, said process comprising:
   providing a connective tissue obtained from an animal in the absence of mincing and/or grinding;
   a porous structure forming step to treat said connective tissue with poring agent in situ to form a porous structure; and
   a washing step to remove impurity from said porous structure thereby obtaining a porous collagen matrix,
   wherein said porous collagen matrix is formed in the absence of a cross-linking process.

2. The process according to claim 1, further comprising a drying step for preserving said porous collagen matrix.

3. The process according to claim 2, wherein said drying step comprises a freezing step, a lyophilizing step, or an air drying step.

4. The process according to claim 1, 2 or 3, further comprising a softening step, wherein said softening step comprises treating said connective tissue with a softening solution.

5. The process according to claim 4, wherein said softening solution is a weak acid solution selected from the group consisting of peracetic acid, hydrochloric acid, oxalic acid, acetic acid and mixtures thereof.

6. The process according to claim 5, wherein said softening solution is acetic acid having a concentration ranging from 0.1 to 6 M.

7. The process according to claim 6, wherein the said softening step comprising
   a first softening step to treat the connective tissue with first acetic acid solution at a concentration ranging from 0.1 to 6M; and
   a second softening step to treat the connective tissue with second acetic acid solution at a concentration ranging from of 0.01 to 2M, said second acetic acid solution further comprising NaCl at a concentration ranging from 0.01 to 4M.

8. The process according to claim 1, 2 or 3, wherein said poring agent is selected from the group consisting of peroxides, peracetic acid, $NaClO_4$, periodic acids, hydriodic acid, trichloromelamine, difluoroacetic acid, chlorine dioxide and mixtures thereof.

9. The process according to claim 8, wherein said poring agent is a solution of hydrogen peroxide having a concentration ranging from 0.1 to 10%.

10. The process according to claim 9, wherein said porous structure forming step is performed under a temperature between 4 and 60° C.

11. The process according to claim 1, 2, or 3, wherein the washing step comprising a first washing step to remove non-collagenous substances with a washing solution which is selected from the group consisting of detergent, chelating agent and mixtures thereof; and a second washing step with enzyme-containing solution to remove impurities which can cause antigenic activity.

12. The process according to claim 11, wherein said detergent is a solution containing SDS having a concentration ranging from 0.01 to 10%; said chelating agent is a solution containing EDTA having a concentration ranging from 0.01 to 100 mM; and said enzyme is a proteolytic enzyme.

13. The process according to claim 4, wherein the washing step comprising a first washing step to remove non-collagenous substances with a washing solution which is selected from the group consisting of detergent, chelating agent and mixtures thereof; and a second washing step with enzyme-containing solution to remove impurities which can cause antigenic activity.

14. The process according to claim 13, wherein said detergent is a solution containing SDS at a concentration ranging from 0.01 to 10%; said chelating agent is a solution containing EDTA at a concentration ranging from 0.01 to 100 mM; and said enzyme is a proteolytic enzyme.

15. The process according to claim 6, wherein the washing step comprising a first washing step to remove non-collagenous substances with a washing solution which is selected from the group consisting of detergent, chelating agent and mixtures thereof; and a second washing step with enzyme-containing solution to remove impurities which can cause antigenic activity.

16. The process according to claim 15, wherein said detergent is a solution containing SDS at a concentration ranging from 0.01 to 10%; said chelating agent is a solution containing EDTA at a concentration ranging from 0.01 to 100 mM; said enzyme is a proteolytic enzyme.

17. The process according to claim 7, wherein the washing step comprising a first washing step to remove non-collagenous substances with a washing solution which is selected from the group consisting of detergent, chelating agent and mixtures thereof; and a second washing step with enzyme-containing solution to remove impurities which can cause antigenic activity.

18. The process according to claim 17, wherein said detergent is a solution containing SDS at a concentration ranging from 0.01 to 10%; said chelating agent is a solution containing EDTA having a concentration ranging from 0.01 to 100 mM; and said enzyme is a proteolytic enzyme.

19. The process according to claim 10, wherein the washing step comprising a first washing step to remove non-collagenous substances with a washing solution which is selected from the group consisting of detergent, chelating agent and mixtures thereof; and a second washing step with enzyme-containing solution to remove impurities which can cause antigenic activity.

20. The process according to claim 19, wherein said detergent is a solution containing SDS at a concentration ranging from 0.01 to 10%; said chelating agent is a solution containing EDTA at a concentration ranging from 0.01 to 100 mM; and said enzyme is a proteolytic enzyme.

* * * * *